(12) United States Patent
Lubinus

(10) Patent No.: US 6,443,992 B2
(45) Date of Patent: Sep. 3, 2002

(54) MILLING TOOL FOR EMPTYING THE FEMORAL MEDULLARY SPACE AND HIP PROSTHESIS TO BE INSERTED IN THE SPACE CREATED

(76) Inventor: Philipp Lubinus, Steenbeker Weg 25, D-24105 Kiel (DE)

( * ) Notice: Subject to any disclaimer, the term of this patent is extended or adjusted under 35 U.S.C. 154(b) by 0 days.

(21) Appl. No.: 09/826,500

(22) Filed: Apr. 4, 2001

Related U.S. Application Data

(62) Division of application No. 09/381,486, filed as application No. PCT/DE98/00763 on Mar. 14, 1998, now Pat. No. 6,283,970.

(30) Foreign Application Priority Data

Mar. 20, 1997 (DE) ......................................... 197 11 532

(51) Int. Cl.[7] .................................................. A61F 2/36
(52) U.S. Cl. .................................. 623/23.18; 623/22.11
(58) Field of Search ......................... 623/22.11, 22.12, 623/22.16, 22.4, 22.41, 22.42, 23.15, 23.17, 23.18, 23.19, 23.24

(56) References Cited

U.S. PATENT DOCUMENTS

| | | | | |
|---|---|---|---|---|
| 3,846,846 A | * | 11/1974 | Fischer | .................... 623/23.18 |
| 4,706,659 A | * | 11/1987 | Mattews et al. | ............... 606/80 |
| 4,878,919 A | * | 11/1989 | Pavansky et al. | ............. 623/23 |
| 6,102,956 A | * | 8/2000 | Kranz | .......................... 623/22 |
| 6,136,035 A | * | 10/2000 | Lob et al. | ...................... 623/23 |

* cited by examiner

Primary Examiner—Jeffrey A. Smith
Assistant Examiner—Michael B. Priddy

(57) ABSTRACT

Milling tool for emptying the femoral medullary space, while creating a space for the shaft of a hip prosthesis, which comprises a flexible core and a plurality of conical, rotationally symmetrical milling segments, mounted in superimposed manner on the core and provided with a central through-bore, the milling segments being so connected to the core and/or the milling segments adjacent thereto, that a rotational force applied to the core and/or the upper segment is transferred to the individual milling segments, as well as a hip prosthesis with a conically directed shaft and a ball mounted on the proximal end of the shaft and which comprises a flexible core, a plurality of conical, rotationally symmetrically segments, mounted in superimposed manner on the core and provided with a central through-bore and a device for tensioning the core to bring a stiffening of the shaft formed from the individual segments.

4 Claims, 2 Drawing Sheets

MILLING TOOL FOR EMPTYING THE FEMORAL MEDULLARY SPACE AND HIP PROSTHESIS TO BE INSERTED IN THE SPACE CREATED

CROSS-REFERENCES TO RELATED APPLICATIONS

This is a Divisional Application of patent application Ser. No. 09/381,486 now U.S. Pat. No. 6,283,970 filed Sep. 20, 1999 of the same inventor which was filed as PCT/DE 98/00763 filed Mar. 14, 1998.

STATEMENT REGARDING FEDERALLY SPONSORED RESEARCH OF DEVELOPMENT

Not applicable.

BACKGROUND OF THE INVENTION

1. Technical Field

This invention relates to a milling tool for emptying the femoral medullary space, whilst creating a space for the shaft or shank of a hip prosthesis and a hip prosthesis suitable for insertion in said space.

The insertion of a hip prosthesis comprising a shaft and a ball to be attached at an angle thereto is a frequent, regularly relatively uncomplicated surgical operation.

However, difficulties arise in those cases in which the femoral medullary space to be emptied with the aid of a milling tool prior to the insertion of the hip prosthesis shaft is not straight, but instead curved, because then when using the conventional, straight milling tools regularly and in undesired manner bony substance to be maintained is also milled off.

2. Background Art

DE 29 14 455 discloses a device for producing a cavity in a bone for the insertion of an artificial joint part, in which two rasp halves adapted to the shape of the bone cavity to be produced are placed on a flexible turning tool drive shaft, the two rasp halves being movable against one another in the axial direction.

WO 94/27507 discloses a milling tool for emptying the femoral medullary space, whilst creating a space for the shaft of a hip prosthesis, having a flexible core and a plurality of conical, rotationally symmetrical milling segments, mounted in superimposed manner on the core and provided with central through-bores, which transfer or transmit a rotational force applied to the core. The pins provided therein for transferring the rotational force shear off, however, on bending the core in non-straight femoral medullary spaces.

SUMMARY OF THE INVENTION

The problem of the invention is to provide a milling tool making it possible to create a space for a hip prosthesis shaft following the path of the femoral medullary space, as well as a hip prosthesis, which can be inserted in such a non-straight, emptied femoral medullary space.

According to the invention this problem is solved by a milling tool for emptying the femoral medullary space, whilst creating a space for the shaft of a hip prosthesis, having a flexible core and a plurality of conical, rotationally symmetrical milling segments, mounted in superimposed manner on the core and provided with central through-bores, which transmit a rotational force applied to the core, and a device for tensioning the core. According to the invention the above-stated problem is also solved by having a hip prosthesis having a conically directed shaft and a ball mounted on the proximal end of the shaft, wherein the hip prosthesis comprises a flexible core, a plurality of conical, rotationally symmetrical segments, mounted in superimposed manner on the core and provided with a central through-bore and a device for tensioning the core bringing about a stiffening of the shaft formed from the individual segments.

BRIEF DESCRIPTION OF THE DRAWINGS

The invention is described in greater detail hereinafter relative to the drawings, wherein.

DETAILED DESCRIPTION OF THE INVENTION

Figure 1:
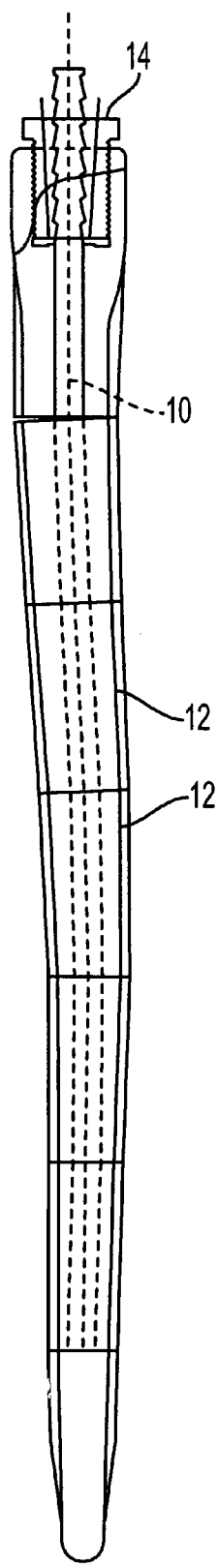
FIG. 1 is diagrammatic representation of such a milling tool in an untensioned core.
Figure 2:
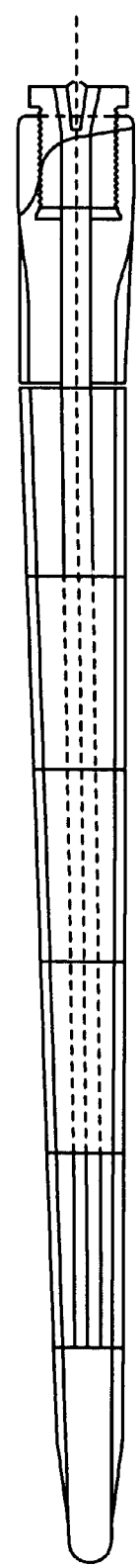
FIG. 2 is representation corresponding to FIG. 1 for a tensioned core.

The milling tool shown in FIGS. 1 and 2 comprises a flexible core and a plurality of conical, rotationally symmetrical milling segments provided with a not shown, central through-bore and mounted in superimposed manner on the core 10.

The core is cross-sectionally noncircular and the through-bore of the milling segments 12 is provided with a correspondingly noncircular, axially directed through-bore (additively or alternatively the end faces of the individual milling segments 12 pointing towards one another can also be provided with meshing radial serrations). The central through bores have wasp waist cross-sections.

The core is provided with a tensioning device 14 acting on the upper milling segment 12 and whose tightening tensions the core 10 against the upper milling segment 12 and consequently beings about a mutual stiffening of the milling segments 12 (and consequently the shaft formed from the individual milling segments 12).

The drawing also shows that the end faces of the milling segments pointing towards one another are slightly convex, so that they can roll on one another.

The lowermost milling segment 12 is firmly attached to the core 10.

For emptying the femoral medullary space the milling tool is attached in the conventional manner with the core 10 untensioned. The distal milling segment 12 (the tip firmly connected to the core 10) will follow the path of the relatively soft femoral medullary space and the following milling segments follow this pate. During the rotation of the milling tool resulting from the application of a rotational force to the core and/or the upper milling segment, they mainly only empty the soft material of the femoral medullary space, thereby protecting the bone. Thus, the milling tool "meanders" through the curved femoral medullary space and empties the same whilst protecting the bone material.

Figure 3:
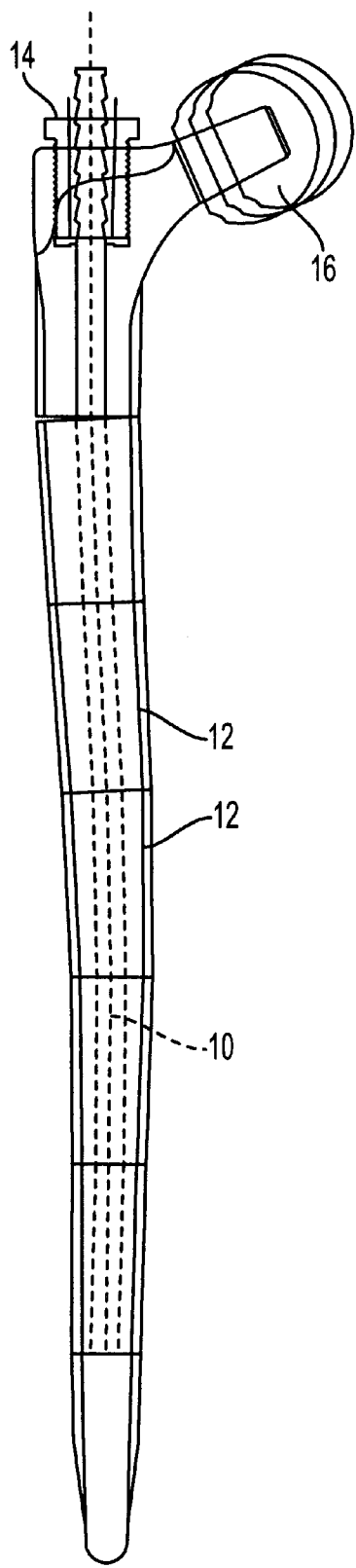
FIG. 3 is hip prosthesis with an untensioned core.
Figure 4:
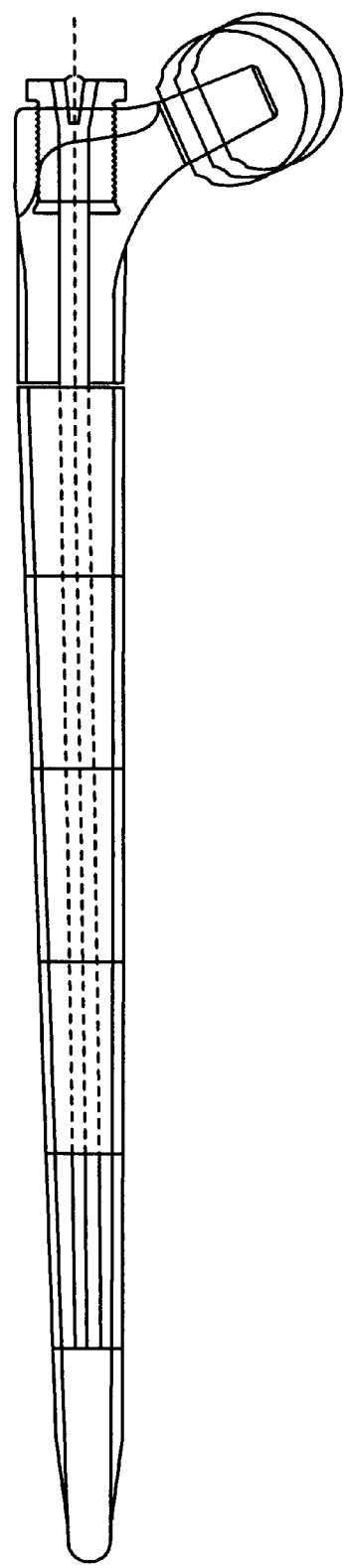
FIG. 4 is representation corresponding to FIG. 3 for a tensioned core.

The hip prosthesis shown in FIGS. 3 and 4 has a corresponding construction. It comprises a flexible core 10, a plurality of conical, rotationally symmetrical segments, mounted in superimposed manner on the core 10 and provided with a central through-bore and a device 14 for tensioning the core 10 bringing about the stiffening of the shaft formed from the individual segments 12.

In the state shown in FIG. 3 in which the core 10 is not tensioned, the hip prosthesis shaft is driven into the previously emptied (not strictly linearly directed) femoral medullary space. During this process the individual segments 12 are so oriented (i.e. tilt with respect to the imaginary shaft axis), that the shaft is adapted to the femoral medullary space.

Following the driving in of the shaft core 10 is tensioned, so that the shaft is stiffened and loaded in the direction of an increasing straightening, which, due to the elasticity of the bone material, leads to a large-area engagement of the segments forming the shaft on the retained bony substance and consequently permits a much greater force transfer of the prosthesis shaft to the femur than would be possible when using a straight shaft.

What is claimed is:

1. Hip prosthesis having a conically directed shaft and a ball (16) mounted on the proximal end of the shaft, characterized in that the hip prosthesis comprises a flexible core (10), a plurality of conical, rotationally symmetrical segments (12), mounted in superimposed manner on the core (10) and provided with a central through-bore and a device (14) for tensioning the core (10) bringing about a stiffening of the shaft formed from the individual segments (12).

2. Hip prosthesis according to claim 1, characterized in that the central through-bore has a wasp waist cross-section.

3. Hip prosthesis according to claim 1, characterized in that the distally positioned segment (12) is firmly attached to the core (10).

4. Hip prosthesis according to claim 1, characterized in that the end faces of the segments (12) are slightly convex.

* * * * *